(12) United States Patent
Yang et al.

(10) Patent No.: US 9,718,724 B2
(45) Date of Patent: Aug. 1, 2017

(54) FUNCTIONAL MATERIAL, ITS PREPARATION METHOD, SEALING MATERIAL, AND DISPLAY PANEL

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Jiuxia Yang, Beijing (CN); Feng Bai, Beijing (CN); Zhenpeng Guo, Beijing (CN); Jing Su, Beijing (CN); Hongbo Feng, Beijing (CN); Jiantao Liu, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

(*) Notice: Subject to any disclaimer, the term of this patent is extended or adjusted under 35 U.S.C. 154(b) by 0 days.

(21) Appl. No.: 14/770,165

(22) PCT Filed: Nov. 21, 2014

(86) PCT No.: PCT/CN2014/091854
§ 371 (c)(1),
(2) Date: Aug. 25, 2015

(87) PCT Pub. No.: WO2016/015410
PCT Pub. Date: Feb. 4, 2016

(65) Prior Publication Data
US 2016/0272535 A1    Sep. 22, 2016

(30) Foreign Application Priority Data

Jul. 29, 2014    (CN) .......................... 2014 1 0367032

(51) Int. Cl.
| | |
|---|---|
| *C08K 9/00* | (2006.01) |
| *C03C 8/24* | (2006.01) |
| *C09C 3/10* | (2006.01) |
| *C09C 1/00* | (2006.01) |
| *C09K 3/10* | (2006.01) |
| *H01L 27/32* | (2006.01) |
| *A61L 9/22* | (2006.01) |
| *C09K 11/02* | (2006.01) |
| *C09K 11/67* | (2006.01) |

(52) U.S. Cl.
CPC ........ *C03C 8/24* (2013.01); *A61L 9/22* (2013.01); *C09C 1/00* (2013.01); *C09C 3/10* (2013.01); *C09K 3/10* (2013.01); *C09K 11/025* (2013.01); *C09K 11/676* (2013.01); *H01L 27/32* (2013.01); *C03C 2204/02* (2013.01); *C03C 2205/00* (2013.01)

(58) Field of Classification Search
CPC ...... C08K 19/56; C08K 11/676; C08K 11/025; C03C 8/24; C03C 2204/62
See application file for complete search history.

(56) References Cited

U.S. PATENT DOCUMENTS

| | | | |
|---|---|---|---|
| 2007/0001608 A1* | 1/2007 | Lee | C03C 8/16 313/587 |
| 2013/0037786 A1* | 2/2013 | Miyao | C08K 9/04 257/40 |
| 2016/0251526 A1* | 9/2016 | Yang | C09C 1/40 522/39 |
| 2016/0251544 A1* | 9/2016 | Yang | C09C 1/40 |
| 2016/0254486 A1* | 9/2016 | Yang | C09C 3/10 |
| 2016/0266395 A1* | 9/2016 | Yang | C09C 3/10 |
| 2016/0280998 A1* | 9/2016 | Yang | C09C 3/10 |
| 2016/0369164 A1* | 12/2016 | Yang | C09C 3/10 |
| 2016/0370531 A1* | 12/2016 | Yang | C09C 3/10 |

FOREIGN PATENT DOCUMENTS

| | | |
|---|---|---|
| CN | 1656148 A | 8/2008 |
| CN | 101805517 A | 8/2010 |
| CN | 102039100 A | 5/2011 |
| CN | 103555003 A | 2/2014 |
| CN | 103739205 A | 4/2014 |

OTHER PUBLICATIONS

International Search Report & Written Opinion Appln. No. PCT/CN2014/091854; Dated May 6, 2015.

* cited by examiner

*Primary Examiner* — Hannah Pak
(74) *Attorney, Agent, or Firm* — Ladas & Parry LLP

(57) ABSTRACT

The present invention provides a functional material and a method for preparing the same, as well as a sealing material and a display panel, which belong to the display technical field and can solve the problem that existing display devices will produce pollution. The functional material of the present invention includes an inorganic powder whose surface has a modified layer, wherein the inorganic powder includes: any one or more of aluminum oxide, magnesium oxide, zinc oxide, zirconium oxide, silicon dioxide, titanium dioxide, boron oxide, diiron trioxide, calcium oxide, potassium oxide, sodium oxide and lithium oxide; the modified layer is generated by a reaction of a dianhydride and a diamine. The sealing material of the present invention includes the above functional material. The display panel of the present invention includes a sealing structure made of the above functional material.

9 Claims, 2 Drawing Sheets

FUNCTIONAL MATERIAL, ITS PREPARATION METHOD, SEALING MATERIAL, AND DISPLAY PANEL

TECHNICAL FIELD

The present invention relates to the display technical field, in particular to a functional material and a method for preparing the same, as well as a sealing material, and a display panel.

BACKGROUND

As shown in FIG. 1, a display panel such as an organic light-emitting diode (OLED) display panel includes two display substrates (for example an array substrate 11 and an encapsulation substrate 12) assembled together, where a sealing structure 2 provided between the two display substrates is outside the display region of the two display substrates, which is used for bonding the two display substrates and preventing external moisture and oxygen from entering the display region to affect a display structure such as an organic light-emitting diode 19. The sealing structure 2 is generally made of a sealing material which typically comprises ingredients such as a low melting point glass powder, a cellulose resin, a solvent, an additive (for example a defoamer, an adhesion promoter) and the like.

However, the existing display devices would inevitably produce certain electromagnetic radiation pollution during use, which will affect human health.

SUMMARY OF THE INVENTION

Regarding the problem that existing display devices would produce pollution, the present invention provides a functional material and a method for preparing the same, as well as a sealing material and a display panel, which can solve the above problem.

One technical solution employed to solve a technical problem of the present invention is a functional material comprising an inorganic powder whose surface has a modified layer, wherein the inorganic powder comprises any one or more of aluminum oxide, magnesium oxide, zinc oxide, zirconium oxide, silicon dioxide, titanium dioxide, boron oxide, diiron trioxide, calcium oxide, potassium oxide, sodium oxide and lithium oxide; and the modified layer is generated by a reaction of a dianhydride and a diamine.

For example, the molar ratio of the dianhydride to the diamine for generating the modified layer is from 0.85:1 to 1.05:1.

Further preferably, the molar ratio of the dianhydride to the diamine for generating the modified layer is from 0.92:1 to 1.05:1.

For example, the dianhydride for generating the modified layer comprises at least one phenyl group, and the diamine for generating the modified layer comprises at least one phenyl ring or at least one non-phenyl six-membered carbocyclic ring.

More preferably, the dianhydride for generating the modified layer is selected from any one of pyromellitic dianhydride, trimellitic anhydride, benzophenone dianhydride, biphenyl dianhydride, diphenyl ether dianhydride, and 4,4'-(hexafluoroisopropylidene) diphthalic anhydride (also named as hexafluoro dianhydride); and the diamine for generating the modified layer is selected from any one of 3-amino-benzyl amine, 2,2'-difluoro-4,4'-(9-fluorenylidene) dianiline, 2,2-bis(3-amino-4-hydroxyphenyl) hexafluoropropane, hexahydro-m-xylylene diamine, 1,4-bis(aminomethyl) cyclohexane, 2,2-bis[4-(4-aminophenoxy)phenyl] hexafluoropropane, 2,2-bis(3-amino-4-methylphenyl) hexafluoropropane, 2,2-bis(3-aminophenyl) hexafluoropropane, 2,2-bis(4-aminophenyl) hexafluoropropane, 2,7-diamino-fluorene, m-xylylene diamine, and 4,4'-methylene bis(2-ethyl-6-methylaniline).

For example, the inorganic powder has a particle diameter of 1 to 5000 nm.

One technical solution employed to solve a technical problem of the present invention is a method for preparing the above functional material, wherein the method comprises:
mixing the inorganic powder, the dianhydride, and the diamine with an initiator and a solvent uniformly; and
reacting the dianhydride with the diamine by heating to form the modified layer on the surface of the inorganic powder.

For example, the mass ratio of the inorganic powder to the substance generated by the reaction of the dianhydride and the diamine is from 20:1 to 1:1.

For example, the heating comprises two stages, specifically: heating at a temperature of 35° C. to 70° C. for 20 to 40 min; and heating at a temperature of 70° C. to 100° C. for 20 to 40 min.

One technical solution employed to solve a technical problem of the present invention is a sealing material comprising: a low melting point glass powder, a cellulose resin; a solvent; and the above functional material.

For example, the sealing material further comprises an additive, and without calculating the mass of the modified layer in the functional material, the mass percentages of the components in the sealing material are:
the low melting point glass powder: 10 to 50%;
the cellulose resin: 10 to 30%;
the solvent: 15 to 75%; and
the additive: 0.2 to 5%.

The expression "without calculating the mass of the modified layer in the functional material, the mass percentage of a certain substance in the sealing material" herein refers to the content of the certain substance in the case that the total mass of all substances in the sealing material (the inorganic powder in the functional material, the cellulose resin, the solvent, the additive and the like) except the modified layer in the functional material is 100%.

For example, without calculating the mass of the modified layer in the functional material, the mass percentage of the inorganic powder in the functional material is 0.1 to 2.5% based on the sealing material.

Preferably, without calculating the mass of the modified layer in the functional material, the mass percentage of the inorganic powder in the functional material is 0.1 to 2.0% based on the sealing material.

More preferably, without calculating the mass of the modified layer in the functional material, the mass percentage of the inorganic powder in the functional material is 0.1 to 1.8% based on the sealing material.

One technical solution employed to solve a technical problem of the present invention is a display panel, comprising a first substrate and a second substrate which are assembled to each other, wherein the first substrate and the second substrate are connected via a sealing structure made of the above sealing material.

The functional material of the present invention can emit far-infrared light and negative ions. Far-infrared light, after being absorbed by a human body, can allow water molecules in the body to resonate and be activated, which enhances the intermolecular bonding force, thereby activating proteins and other biological macromolecules and bringing the organism cells to the highest vibration level. Furthermore, far-infrared heat can be transferred to a subcutaneous deeper part, thus increasing the temperature of the subcutaneous deeper part, expanding the capillaries, promoting the blood circulation, strengthening the metabolism among tissues, promoting a tissue regeneration capacity, enhancing the organism immunity, and bringing the vivacity. On the other hand, negative ions can decompose and oxidize bacteria and organic substances, and may serve the function of disinfection and sterilization and produce the effect of improving air quality. Therefore, the functional material may play a role in health care and is environmentally friendly.

The surface of the inorganic powder in the functional material of the present invention has a modified layer which can allow the inorganic powder to be well incorporated into a sealing structure and can improve the inorganic powder's capacity to emit far-infrared light and negative ions.

The sealing structure of the display panel according to the present invention comprises the above functional material, and therefore can constantly emit far-infrared light and negative ions during use and is environmentally friendly.

Figure 1:
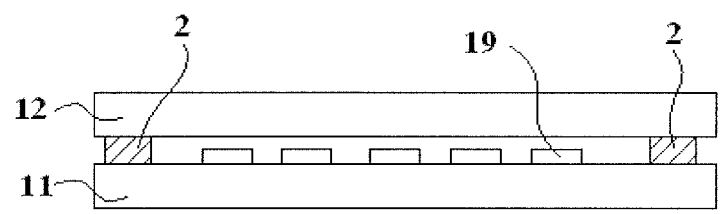
FIG. 1 is a schematic cross-sectional structure of an existing display panel.

wherein, the reference signs are:

11. an array substrate; 12. an encapsulation substrate; 19. an organic light emitting diode; and 2. a sealing structure.

DETAILED DESCRIPTION

To enable those skilled in the art to better understand the technical solution of the present invention, further detailed descriptions are made for the present invention with reference to the drawings and embodiments.

The present embodiment provides a functional material and a method for preparing the same.

The functional material comprises an inorganic powder whose surface has a modified layer, wherein the inorganic powder comprises any one or more of aluminum oxide, magnesium oxide, zinc oxide, zirconium oxide, silicon dioxide, titanium dioxide, boron oxide, diiron trioxide, calcium oxide, potassium oxide, sodium oxide and lithium oxide; and the modified layer is generated by a reaction of a dianhydride and a diamine.

The particle diameter of the inorganic powder is from nanometers to micrometers, specifically, for example, from 1 to 5000 nm, preferably from 10 to 500 nm. The particle diameter can be measured, for example by a Malvern laser particle size analyzer.

Dianhydride herein refers to a substance containing at least two anhydride groups in the molecular structure; while diamine herein refers to a substance containing at least two amine groups (or amino groups) in the molecular structure.

The dianhydride, for example, contains at least one phenyl group, and is preferably any one of pyromellitic dianhydride, trimellitic anhydride, benzophenone dianhydride, biphenyl dianhydride, diphenyl ether dianhydride, and 4,4'-(hexafluoroisopropylidene) diphthalic anhydride (also named as hexafluoro dianhydride).

The diamine, for example, contains at least one phenyl ring or at least one non-phenyl six-membered carbocyclic ring (e.g. cyclohexyl), and is preferably any one of 3-aminobenzyl amine, 2,2'-difluoro-4,4'-(9-fluorenylidene) dianiline, 2,2-bis(3-amino-4-hydroxyphenyl) hexafluoropropane, hexahydro-m-xylylene diamine, 1,4-bis(aminomethyl) cyclohexane, 2,2-bis[4-(4-aminophenoxy)phenyl]hexafluoropropane, 2,2-bis(3-amino-4-methylphenyl) hexafluoropropane, 2,2-bis(3-aminophenyl) hexafluoropropane, 2,2-bis(4-aminophenyl) hexafluoropropane, 2,7-diaminofluorene, m-xylylene diamine, and 4,4'-methylene bis(2-ethyl-6-methylaniline).

The molar ratio of the dianhydride to the diamine is from 0.85:1 to 1.05:1, preferably from 0.92:1 to 1.05:1.

Our study revealed that the modified layer generated by the reaction of the above dianhydride and diamine can desirably improve the properties of the inorganic powder.

Functional materials of the present embodiment can emit far-infrared light and negative ions. Far-infrared light, after being absorbed by a human body, can allow water molecules in the body to resonate and be activated, which enhances the intermolecular bonding force, thereby activating proteins and other biological macromolecules and bringing the organism cells to the highest vibration level. Furthermore, far-infrared heat can be transferred to a subcutaneous deeper part, thus increasing the temperature of the subcutaneous deeper part, expanding the capillaries, promoting the blood circulation, strengthening the metabolism among tissues, promoting a tissue regeneration capacity, enhancing the organism immunity, and bringing the vivacity. On the other hand, negative ions can decompose and oxidize bacteria and organic substances, and may serve the function of disinfection and sterilization and produce the effect of improving air quality. Therefore, the functional material may play a role in health care and is environmentally friendly.

The method for preparing the above functional material comprises: mixing the inorganic powder, the dianhydride, and the diamine with an initiator and a solvent uniformly; and reacting the dianhydride with the diamine by heating to form the modified layer on the surface of the inorganic powder.

Figure 2:
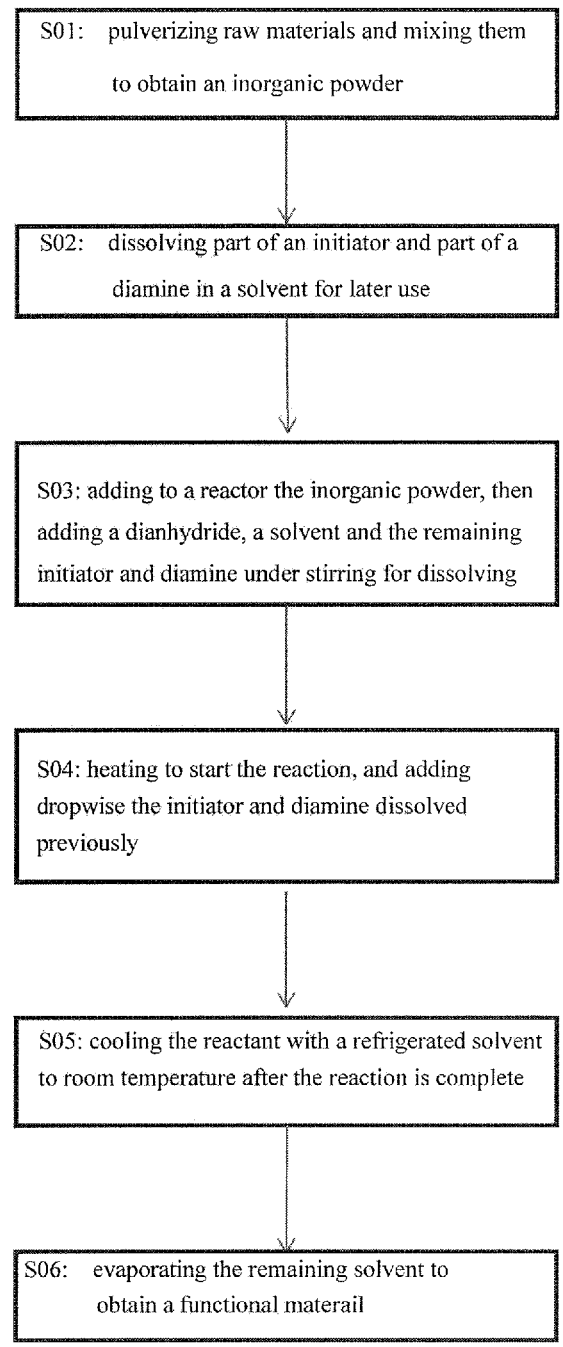
FIG. 2 is a flow chart of the method for preparing the functional material according to an embodiment of the present invention.

Specifically, as shown in FIG. 2, the above preparation method may comprise:

S01, in the case of using a dispersant, pulverizing various materials into powder respectively and then uniformly mixing them proportionally, or uniformly mixing various materials proportionally and then pulverizing them, to yield an inorganic powder.

The dispersant may be chosen from conventional dispersants such as BYK 161 manufactured by BYK Additives & Instruments and Solsperse 32500 and Solsperse 22000 manufactured by The Lubrizol Corporation. Pulverization may be carried out using conventional methods such as ball milling, grinding, and the like. As the inorganic powder may be prepared by existing methods, no further details will be provided herein.

S02, dissolving from a fourth to a third of an initiator and from a fourth to a third of a diamine in a solvent for later use.

The mass ratio of the inorganic powder to the substance generated by the reaction of the dianhydride and the diamine is from 20:1 to 1:1.

That is to say, the amounts of the dianhydride and the diamine are determined according to the following manner assuming a complete reaction between the dianhydride and the diamine to yield a resultant (which is actually a modified layer), if the mass of the resultant is 1, then the mass of the inorganic powder will be between 1 and 20; such an amount can ensure that a modifier layer with a suitable thickness can be obtained on the inorganic powder.

An initiator is used to initiate the reaction, which, for example, is a nitrogen-based initiator, preferably any one of azo bisisobutyronitrile, 2,2'-azo bis(2,4-dimethylvaleronitrile), dimethyl azo bisisobutyrate, and azo bisisovaleronitrile.

The solvent can be selected from fatty alcohols, glycol ethers, ethyl acetate, methyl ethyl ketone, methyl isobutyl ketone, ethylene glycol monomethyl ether ester, γ-butyrolactone, ethyl 3-ethoxypropionate, butyl carbitol, butyl carbitol acetate, propylene glycol monomethyl ether, propylene glycol monomethyl ether acetate, cyclohexane, xylene, isopropanol, and other conventional organic solvents. Since the solvent merely serves to disperse various substances, propylene glycol monomethyl ether acetate is used as a solvent in the process of specifically preparing the functional material in all the Examples.

S03, adding the inorganic powder to a reaction vessel (e.g., a four-neck flask) which is then subjected to stirring, shocking, shaking and the like; afterwards, adding the dianhydride and the solvent as well as the remaining initiator and diamine and allowing them to be dissolved uniformly.

S04, heating to carry out the reaction, preferably in two stages, specifically comprising: heating at a temperature of 35° C. to 70° C. for 20 to 40 min; and then continuing heating at a temperature of 70 to 100° C. for 20 to 40 min During the above heating process, the dianhydride and the diamine are allowed to react, thereby generating a modified layer on the surface of the inorganic powder, wherein heating is carried out in two stages so as to prevent the reaction from being too severe.

During the reaction process, the above solution prepared by dissolving an initiator and a diamine is gradually added dropwise to a four-neck flask so as to prevent the reaction from being too severe.

The reaction in this step may be carried out, for example, under the protection of nitrogen, and for example under constant stirring.

The solvent in each step is in an amount sufficient to disperse and dissolve the substances therein uniformly, and the initiator is in an amount sufficient to initiate the reaction. These amounts can be adjusted by those skilled in the art based on the actual conditions, and thus no further detail is given herein. However, generally speaking, the mass ratio (referring to the total amount) of the inorganic powder, the initiator and the solvent is 1:(0.25 to 0.4):(1 to 1.5). To achieve consistency in the process of preparing the functional material in the various Examples, the mass ratio of the inorganic powder, the initiator and the solvent is 1:0.3:1.4.

S05, cooling the reactant with a refrigerated solvent to room temperature (about 10 to 30° C.) after the reaction is over.

S06, evaporating the remaining solvent or separating the powder therefrom to yield an inorganic powder with a modified layer, i.e., a functional material.

Of course, it should be appreciated that the preparation method described above may also undergo many changes, for example, the dianhydride, the diamine, the initiator and the like can all be dissolved in a solvent once; for another example, heating can be carried out at only one stage. After all, any variation is allowed as long as the dianhydride and the diamine can react to form a modified layer on the surface of the inorganic powder.

The present embodiment further provides a sealing material, comprising: a low melting point glass powder, a cellulose resin; a solvent; and the above functional material.

The sealing material is used for forming a sealing structure in a display panel so as to connect two display substrates and prevent moisture and oxygen from entering the display region.

For example, the sealing material further comprises an additive(s), and without calculating the mass of the modified layer in the functional material, the mass percentages of the components in the sealing material are:
the low melting glass powder 10 to 50%;
the cellulose resins: 10 to 30%;
the solvent: 15 to 75%; and
the additive(s): 0.2 to 5%.

That is to say, the contents of the components are as above in the case that the total mass of all substances in the sealing material (the inorganic powder in the functional material, the cellulose resin, the solvent, the additive and the like) except the modified layer in the functional material is 100%.

The low melting point glass herein is the primary ingredient for forming a sealing structure, which can be boron oxide-zinc oxide-vanadium oxide glass, vanadium oxide-zinc oxide-barium oxide glass or the like and have a particle diameter of 500 nm to 6 μm.

The cellulose resin herein is used as a carrier material for preliminarily curing the sealing material into a desired shape so as to form a sealing structure. Specifically, the cellulose resin may be selected from methyl cellulose, ethyl cellulose, carboxyethyl cellulose, carboxymethyl cellulose, carboxymethyl hydroxyethyl cellulose and the like, and is preferably in an amount of 10 to 25%, more preferably 10 to 20%.

The sealing material further comprises the above functional material, and therefore the sealing structure prepared therefrom can emit far-infrared light and negative ions. Without calculating the mass of the modified layer in the functional material, the mass percentage of the inorganic powder in the functional material is 0.1 to 2.5%, preferably 0.1 to 2%, more preferably 0.1 to 1.8% based on the sealing material.

The additive herein is used for improving various properties of the sealing material and may comprise an adhesion promoter, a defoamer, a wetting leveling agent and the like.

The solvent is used for dissolving and dispersing other components to form a uniform and stable system, and can be a conventional organic solvent such as ketone, ester, ether, aliphatic hydrocarbon, cycloalkane, aromatic hydrocarbon or the like.

The functional material of the various Examples was prepared using the above preparation method according to the parameters in the following table.

TABLE 1

Relevant parameters of the functional material (content unit: by mass parts)

| Example # | | 1 | 2 | 3 | 4 | 5 | 6 |
|---|---|---|---|---|---|---|---|
| Inorganic powder | aluminum oxide amount | 0.002 | 0.01 | 0.014 | 0.914 | 0.019 | 0.029 |
| | titanium oxide Amount | 0.056 | 0.224 | 0.337 | 0.337 | 0.449 | 0.673 |

TABLE 1-continued

| Relevant parameters of the functional material (content unit: by mass parts) | | | | | | | |
|---|---|---|---|---|---|---|---|
| | zirconium oxide amount | 0.021 | 0.084 | 0.126 | 1.126 | 0.168 | 0.252 |
| | silicon oxide amount | 0.019 | 0.04 | 0.06 | 0.06 | none | 0.12 |
| | boron oxide amount | none | 0.024 | 0.036 | 0.036 | 0.128 | 0.072 |
| | diiron trioxide amount | none | 0.012 | 0.018 | 0.018 | 0.024 | 0.036 |
| | sodium oxide amount | 0.002 | 0.006 | 0.009 | 0.009 | 0.012 | 0.018 |
| Total amount | | 0.1 | 0.4 | 0.6 | 2.5 | 0.8 | 1.2 |
| Type of dianhydride | | pyromellitic dianhydride | pyromellitic dianhydride | diphenyl ether dianhydride | pyromellitic dianhydride | diphenyl ether dianhydride | hexafluoro dianhydride |
| Type of diamine | | 3-amino benzylamine | hexahydro-m-xylylene diamine | m-xylylene diamine | 3-amino benzylamine | hexahydro-m-xylylene diamine | 3-amino benzylamine |
| Molar ratio of dianhydride to diamine | | 0.85 | 0.87 | 0.92 | 1 | 1.05 | 1.05 |
| Mass ratio of inorganic powder to reaction product | | 20 | 10 | 8 | 15 | 1 | 4 |
| Initiator for preparing the function material | | Azodiiso butyronitrile | Azodiiso butyronitrile | Azobisiso valeronitrile | Azobisiso valeronitrile | Azodiiso butyronitrile | Azodiiso butyronitrile |
| Heating temp. at the 1st stage (° C.) | | 35 | 40 | 70 | 60 | 50 | 55 |
| Heating time at the 1st stage (min) | | 40 | 40 | 20 | 25 | 30 | 25 |
| Heating temp. at the 2nd stage (° C.) | | 75 | 85 | 75 | 80 | 70 | 90 |
| Heating time at the 2nd stage (min) | | 40 | 25 | 30 | 35 | 40 | 30 |

| | | Example # | 7 | 8 | 9 | 10 |
|---|---|---|---|---|---|---|
| | Inorganic powder | aluminum oxide amount | 0.024 | 0.829 | 0.043 | 0.033 |
| | | titanium oxide Amount | 0.561 | 0.673 | none | 0.785 |
| | | zirconium oxide amount | 0.21 | 0.252 | 0.378 | 0.294 |
| | | silicon oxide amount | 0.115 | 0.12 | 1.19 | 0.14 |
| | | boron oxide amount | 0.06 | 0.072 | 0.108 | 0.084 |
| | | diiron trioxide amount | 0.03 | 0.036 | 0.054 | 0.042 |
| | | sodium oxide amount | none | 0.018 | 0.027 | 0.022 |
| | | Total amount | 1 | 2 | 1.8 | 1.4 |
| | Type of dianhydride | | hexafluoro dianhydride | diphenyl ether dianhydride | hexafluoro dianhydride | hexafluoro dianhydride |
| | Type of diamine | | m-xylylene diamine | 2,7-diamino fluorene | m-xylylene diamine | 2,7-diamino fluorene |
| | Molar ratio of dianhydride to diamine | | 1 | 0.9 | 0.9 | 0.85 |
| | Mass ratio of inorganic powder to reaction product | | 20 | 1 | 7.5 | 16 |
| | Initiator for preparing the function material | | Dimethyl azobis isobutyrate | Azodiiso butyronitrile | Azobisiso valeronitrile | Azobisiso valeronitrile |
| | Heating temp. at the 1st stage (° C.) | | 55 | 65 | 70 | 35 |
| | Heating time at the 1st stage (min) | | 30 | 35 | 35 | 35 |
| | Heating temp. at the 2nd stage (° C.) | | 90 | 100 | 95 | 70 |
| | Heating time at the 2nd stage (min) | | 20 | 20 | 25 | 35 |

A sealing material was formulated using the functional material according to the ratio in the following table. There was no need to employ a specific adding sequence and a specific mixing method as long as various components can be mixed uniformly.

In Examples, vanadium oxide-boron oxide-zinc oxide glass was selected as the low melting point glass; Ethyl Cellulose A186 was selected as the cellulosic resin; diethylene glycol butyl ether acetate was selected as the solvent; and the defoamer BYK-A555 was selected as the additive.

All the components in the sealing materials except the functional material were conventional materials, and therefore the sealing materials shared these components to achieve comparability of the results.

Afterwards, the sealing material was applied to the desired region of the substrate by a screen printing process, and then sintered at a temperature of 380° C. for 90 min, so that the sealing material was preliminarily cured. Next, another substrate was assembled thereto, and the preliminarily cured sealing material was irradiated with laser to allow it melt, thereby forming a sealing structure having a thickness of 5 μm and a width of 700 μm.

Subsequently, the infrared emissivity of the sealing structure was measured according to the GB/T 7287-2008 standard, and the amount of negative ions produced thereby was measured using an air anion analyzer (for example, Japanese KEC Corporation's KEC-900 type). The sealing cross-section of the sealing structure was observed using a scanning electron microscope.

The present embodiment further provides a display panel, comprising a first substrate (e.g., an array substrate) and a second substrate (e.g., an encapsulation substrate) which are assembled to each other.

The first substrate and the second substrate were connected to each other via a sealing structure. The sealing structure located between the two display substrates was outside the display region of the two display substrates and can prevent moisture, oxygen and the like from entering the display region.

The sealing structure was made of the above sealing material. Specifically, the sealing material was applied onto an encapsulation substrate by means of a process such as screen printing process, sintered for preliminary curing, then assembled with an array substrate, and irradiated with laser to allow it melt so as to form the sealing structure. Alternatively, the sealing material was removed from the substrate after preliminary curing, processed into a suitable shape like strips, disposed at a desired position, and then melted by irradiation with laser.

The specific method for forming a sealing structure is known, and therefore no further detail will be given herein. However, generally speaking, curing was carried out at a temperature of 280° C. to 550° C. for a time period of 50 to 120 min; the parameters of laser radiation can be determined according to the material and apparatus; the sealing structure finally obtained generally had a thickness of 3.5 μm to 5.5 μm and a width of 500 μm to 1.0 mm.

It should be appreciated that the above embodiments are merely exemplary embodiments to illustrate the principles

TABLE 2

Relevant parameters of the sealing material and the sealing structure (content unit: by mass parts)

| Example | 1 | 2 | 3 | 4 | 5 | 6 | 7 | 8 | 9 | 10 |
|---|---|---|---|---|---|---|---|---|---|---|
| Amount of inorganic powder in the functional material | 0.1 | 0.4 | 0.6 | 2.5 | 0.8 | 1.2 | 1 | 2 | 1.8 | 1.4 |
| Amount of low melting point glass powder | 45 | 12 | 38 | 40 | 35 | 38 | 40 | 45 | 40 | 43 |
| Amount of cellulosic resin | 30 | 14 | 20 | 25 | 19 | 20 | 25 | 28 | 25 | 25 |
| Amount of solvent | 19.9 | 68.6 | 37.4 | 32.3 | 41.7 | 39 | 31.2 | 24.5 | 32.4 | 29.4 |
| Amount of additive | 5 | 5 | 4 | 0.2 | 3.5 | 1.8 | 2.8 | 0.5 | 0.8 | 1.2 |
| Far-Infrared emissivity (%) | 50 | 62 | 83 | 96 | 91 | 93 | 92 | 95 | 94 | 92 |
| Anion concentration (/cm$^3$) | 135 | 480 | 765 | 2100 | 950 | 1510 | 1100 | 1980 | 1820 | 1600 |
| State of sealing cross-section | compact | compact | compact | compact | compact | compact | compact | compact | compact | compact |

It can be seen that all the sealing materials in Examples had high infrared emissivity and anion concentration, which indicated that they can produce far-infrared light and negative ions, thereby improving the environment. Meanwhile, the sealing cross-section of the sealing structure was compact, which indicated that the sealing properties were excellent and that incorporation of the functional material did not produce any adverse effects on its own properties.

The surface of the inorganic powder of the functional material in the present embodiment had a modified layer capable of allowing the inorganic powder to be well incorporated into the sealing structure and improving the inorganic powder's capacity to emit far-infrared light and negative ions.

of the present invention, but the present invention is not limited thereto. Those of ordinary skill in the art, without departing from the spirit and essence of the present invention, may make various changes and improvements. Such changes and improvements are deemed within the scope of the invention.

The present application claims the priority of the Chinese Patent Application No. 201410367032.5 filed on Jul. 29, 2014, which is incorporated herein by reference as part of the present application.

What is claimed is:
1. A sealing material, comprising:
a low melting point glass powder which is boron oxide-zinc oxide-vanadium oxide glass powder, or vanadium oxide-zinc oxide-barium oxide glass powder;

a cellulose resin;

a solvent; and a functional material comprising an inorganic powder whose surface has a modified layer, wherein the inorganic powder comprises any one or more of aluminum oxide, magnesium oxide, diiron trioxide, calcium oxide, potassium oxide, sodium oxide and lithium oxide; and the modified layer is generated by a reaction of a dianhydride and a diamine, wherein the sealing material further comprises an additive(s), and without calculating the mass of the modified layer in the functional material, the mass percentages of the components in the sealing material are:

the low melting point glass powder: 10 to 50%;

the cellulose resin: 10 to 30%;

the solvent: 15 to 75%; and the additive(s): 0.2 to 5%.

2. The sealing material according to claim 1, wherein without calculating the mass of the modified layer in the functional material, the mass percentage of the inorganic powder in the functional material is 0.1 to 2.5% based on the sealing material.

3. The sealing material according to claim 2, wherein without calculating the mass of the modified layer in the functional material, the mass percentage of the inorganic powder in the functional material is 0.1 to 2% based on the sealing material.

4. The sealing material according to claim 3, wherein without calculating the mass of the modified layer in the functional material, the mass percentage of the inorganic powder in the functional material is 0.1 to 1.8% based on the sealing material.

5. The sealing material according to claim 1, wherein the molar ratio of the dianhydride to the diamine for generating the modified layer is between 0.85:1 and 1.05:1.

6. The sealing material according to claim 5, wherein the molar ratio of the dianhydride to the diamine for generating the modified layer is between 0.92:1 and 1.05:1.

7. The sealing material according to claim 1, wherein the dianhydride for generating the modified layer comprises at least one phenyl group; and the diamine for generating the modified layer comprises at least one phenyl ring or at least one non-phenyl six-membered carbocyclic ring.

8. The sealing material according to claim 7, wherein the dianhydride for generating the modified layer is selected from any one of pyromellitic dianhydride, trimellitic anhydride, benzophenone dianhydride, biphenyl dianhydride, diphenyl ether dianhydride, and 4,4'-(hexafluoroisopropylidene)diphthalic anhydride; and the diamine for generating the modified layer is selected from any one of 3-amino benzylamine, 2,2'-difluoro-4,4'-(9-fluorenylidene) dianiline, 2,2-bis(3-amino-4-hydroxyphenyl) hexafluoropropane, hexahydro-m-xylylene diamine, 1,4-bis(aminomethyl) cyclohexane, 2,2-bis[4-(4-aminophenoxy)phenyl] hexafluoropropane, 2,2-bis(3-amino-4-methylphenyl) hexafluoropropane, 2,2-bis(3-aminophenyl) hexafluoropropane, 2,2-bis(4-aminophenyl) hexafluoropropane, 2,7-diamino fluorene, m-xylylene diamine, and 4,4'-methylene bis (2-ethyl-6-methylaniline).

9. The sealing material according to claim 1, wherein the inorganic powder has a particle diameter of 1 to 5000 nm.

* * * * *